US 8,426,615 B2

United States Patent
Mariage et al.

(10) Patent No.: US 8,426,615 B2
(45) Date of Patent: Apr. 23, 2013

(54) METHOD OF OBTAINING LACTIDE

(75) Inventors: Pierre-Antoine Mariage, Escanaffles (BE); Delphine Hottois, Escanaffles (BE); Philippe Coszach, Escanaffles (BE)

(73) Assignee: Futerro S.A., Escanaffles (BE)

( * ) Notice: Subject to any disclaimer, the term of this patent is extended or adjusted under 35 U.S.C. 154(b) by 72 days.

(21) Appl. No.: 13/056,028

(22) PCT Filed: Aug. 13, 2009

(86) PCT No.: PCT/EP2009/060501
§ 371 (c)(1),
(2), (4) Date: Apr. 19, 2011

(87) PCT Pub. No.: WO2010/018209
PCT Pub. Date: Feb. 18, 2010

(65) Prior Publication Data
US 2011/0190512 A1    Aug. 4, 2011

(30) Foreign Application Priority Data
Aug. 14, 2008 (BE) .................................. 2008/0450

(51) Int. Cl.
*C07D 319/00* (2006.01)
(52) U.S. Cl.
USPC .......................................................... 549/274
(58) Field of Classification Search ................... 549/274
See application file for complete search history.

(56) References Cited

U.S. PATENT DOCUMENTS

| 5,214,159 | A | | 5/1993 | Muller et al. | |
|---|---|---|---|---|---|
| 5,319,107 | A | * | 6/1994 | Benecke et al. | 549/274 |
| 5,463,086 | A | * | 10/1995 | Kubota et al. | 549/274 |
| 6,313,319 | B1 | * | 11/2001 | Ohara et al. | 549/274 |

* cited by examiner

Primary Examiner — Nizal Chandrakumar

(57) ABSTRACT

The present invention relates to a method of obtaining lactide by means of a solvent of the ether class from a mixture that is in liquid form comprising lactide, meso-lactide, and other impurities.

20 Claims, 1 Drawing Sheet

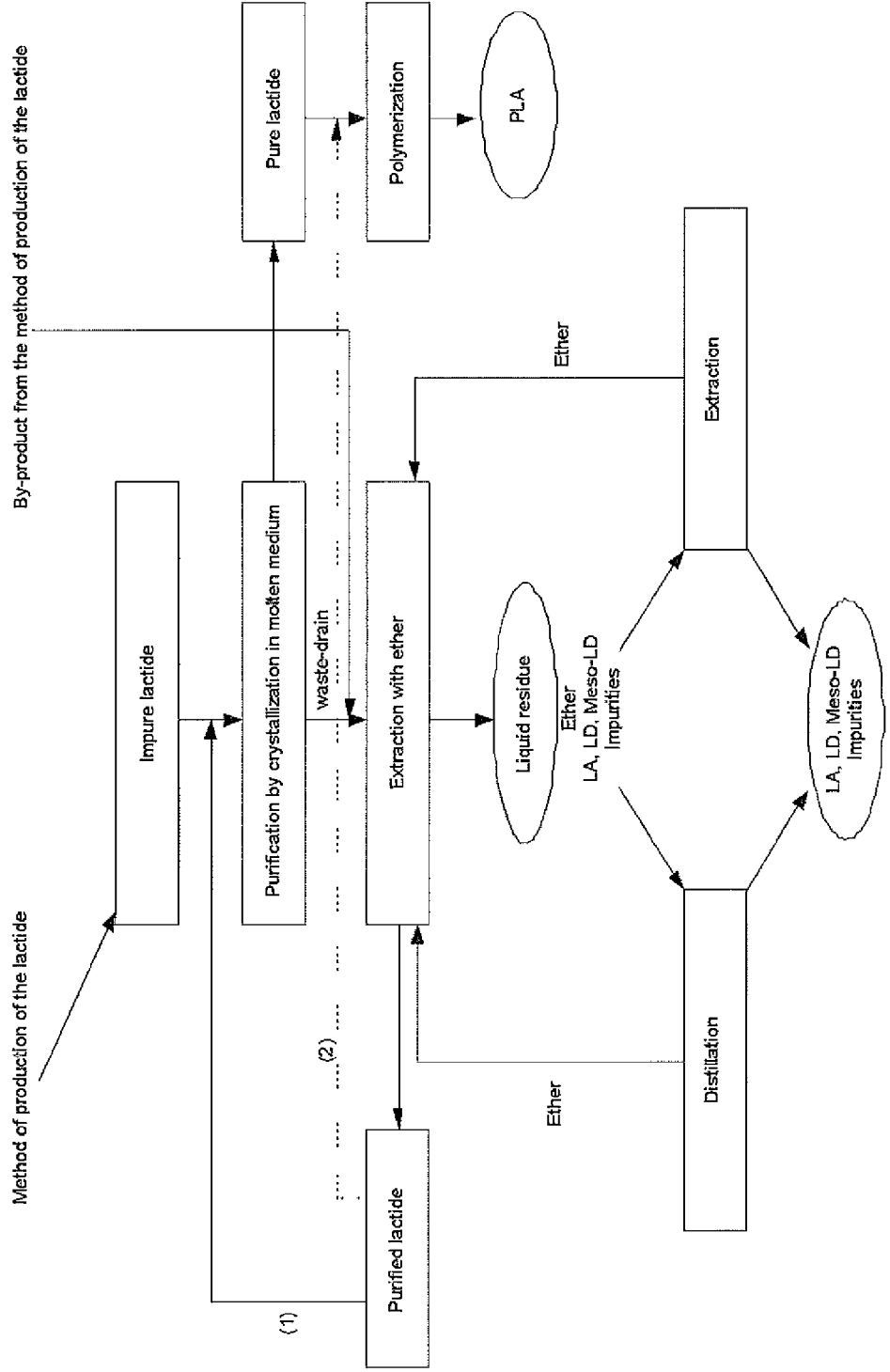

METHOD OF OBTAINING LACTIDE

The present invention relates to a method of obtaining lactide by means of a solvent from the ether class starting from a mixture that is in liquid form comprising lactide, meso-lactide and other impurities.

The development of bioplastics is now expanding rapidly. The use of bioplastics such as for example polylactide (PLA) in the packaging field is steadily increasing.

PLA is an aliphatic polyester based on lactic acid, the latter being obtained by fermentation of sugars and/or starch. Polylactide is therefore derived from renewable vegetable resources and is biodegradable by composting.

PLA can be produced starting from the cyclic dimer of lactic acid called lactide.

The two optically active forms of lactic acid (L-LA) and (D-LA) can give a lactide (LD or cyclic dimer) in 3 stereoisomeric forms: with 2 molecules of D-lactic acid (D,D-lactide or D-LD), with 2 molecules of L-lactic acid (L,L-lactide or L-LD) or with one molecule of each (meso-lactide or meso-LD). There is also the racemic mixture ((D,L)-lactide), characterized by a melting point (m.p.=126° C.) above that of L-LD or D-LD (m.p.=97° C.) and above that of meso-LD (m.p.=50° C.)

At present, the 2 main methods of production of lactide differ essentially by the average degree of polymerization (DP) of the oligomers from the condensation stage.

The first method consists of extracting the water from a solution of lactic acid until oligomers are obtained with $8 \leq DP \leq 25$. Then these oligomers are depolymerized (back-biting reaction) with a Lewis acid catalyst, either under reduced pressure at more or less elevated temperature, or under a nitrogen stream. This process is carried out in harsh conditions that affect the optical purity of the lactide (high percentage of racemization).

The second method uses an oligomer with $1.5 \leq DP \leq 2.5$ produced in the vapour phase at elevated temperature or in the liquid phase in the presence of a co-solvent forming an azeotrope with water. The main drawbacks are the presence of a solvent, which is often aromatic and with a high boiling point, a reaction temperature above 180° C., lack of selectivity and a non-negligible level of impurities.

Generally, the lactide obtained by various routes of synthesis must be purified in order to obtain sufficient purity before proceeding to its ring-opening polymerization.

These stages of synthesis and purification therefore lead to the formation of an economically important amount of by-products containing L-lactide, D-lactide, meso-lactide, racemic mixture ((D,L)-lactide), lactic acid, other oligomers of lactic acid, products of thermal degradation of lactic acid and other impurities that are more specific to the processes of synthesis of the lactide, for example 2-ethyl-hexanoic acid resulting from the degradation of tin octanoate, which can be used as a catalyst for lactide synthesis.

These by-products can be:
hydrolysed so as to recover the lactic acid present, and the solution can be recycled upstream of the lactide synthesis. This requires repeating the whole process, which is not advantageous from the standpoint of energy efficiency and therefore is not economic.
extracted with water. As the lactide is not soluble, it precipitates and can be recovered after filtration and drying. This is disclosed in document EP 1 276 735. However, the lactide forms a complex with water, which gradually degrades to a dimer of lactic acid. This leads on the one hand to a large loss of yield and, on the other hand, causes insufficient purity of the lactide after drying (contamination with lactoyl-lactic acid). Moreover, the oligomers of lactic acid larger than 2 units are also sparingly soluble in water and although they are liquid, their filterability is still low owing to their viscosity;
extracted with more or less nonpolar organic solvents such as toluene, ethyl acetate or mixtures thereof. However, during extraction, the amount of impurities dissolved is a function of the polarity and of the solvent/by-product ratio. When the fraction of impurity in the by-product increases, it is necessary to use a solvent of higher polarity and/or a larger fraction of the solvent to avoid exceeding the saturation threshold of the extraction phase. On increasing the polarity and/or the amount of the extraction phase, the amount of lactide that dissolves increases and the loss is greater. Accordingly, as the by-product becomes poorer in lactide (and therefore richer in impurities), the more the loss of lactide by this type of solvent increases and the more the yield decreases.

The present invention overcomes these drawbacks while permitting the lactide to be obtained starting from by-products at an industrially acceptable yield.

FIG. 1 shows a flow sheet of one embodiment of the invention.

"Lactide" means the cyclic diester of lactic acid represented by the following general formula:

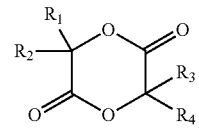

in which $R_1=R_3=H$ and $R_2=R_4=CH_3$.

In the present invention, lactide means one of the two stereoisomeric forms (L-LD or D-LD) and not the meso-LD.

The aim of the present invention is to provide a method of obtaining lactide, more particularly of L-lactide or of D-lactide, from a mixture that is in liquid form comprising lactide, meso-lactide, and other impurities by means of a solvent from the ether class.

Document U.S. Pat. No. 5,214,159 discloses a method for the production of the meso-lactide starting from a mixture of the meso-lactide and D,L-lactide. The mixture is precipitated in crystalline form in an alcohol. The crystals of the meso-lactide and of the D,L-lactide obtained are then recrystallized in the alcohol and then dissolved in an aliphatic ether. The D,L-lactide crystallizes in the ether. The mother liquor that remains, consisting of a mixture of the meso-lactide and D,L-lactide at a ratio of about 60/40, is concentrated by evaporation and the residue is submitted to distillation. This document does not disclose precipitation of the lactide in the ether starting from an impure lactide present in liquid form.

Carothers et al. disclose, in the Journal of American Chemistry Society, volume 54, 1932, pages 761-772, the purification of the lactide by crystallization in the ether. This document does not disclose precipitation of the lactide in the ether starting from an impure lactide present in liquid form.

EP 0 588 222 discloses a method for separating lactide from meso-lactide by washing an impure lactide present in solid form with ether. This document does not disclose precipitation of the lactide in the ether starting from an impure lactide present in liquid form.

U.S. Pat. No. 5,463,086 discloses in comparative example 4 a method for separating L-lactide from meso-lactide by dissolving the raw lactide (2.19 g) in diethyl ether (41.43 g)

followed by crystallization. This document does not disclose precipitation of lactide in the ether starting from an impure lactide in liquid form and ether that are present in the proportions of the present invention.

U.S. Pat. No. 5,319,107 discloses, in examples 1 and 2, the dissolution of a residue of lactide, lactic acid and oligomers in diethyl ether followed by crystallization of the lactide by incubation of the solution at 4° C. A lactide of purity above 90%, or even above 95% was obtained at a yield of 13%. This document does not disclose precipitation of lactide starting from an impure lactide present in liquid form.

The present invention provides a method of obtaining lactide starting from a mixture that is in liquid form comprising lactide, meso-lactide and other impurities, said method comprising the following stages:
  (a) addition of an ether to the mixture, characterized in that said mixture and the ether are both in liquid form at the temperature of mixing and in that the ether is added to the mixture in an ether/mixture weight ratio in the range from 0.5:1 to 10:1,
  (b) optional cooling of the mixture and of the ether at the end of stage (a),
  (c) precipitation of a purified lactide in a liquid phase,
  (d) separation of the mixture obtained from stage (c), and obtention of a moist cake rich in lactide and a liquid phase.

The method of the invention can be used for obtaining both D-lactide and L-lactide.

The mixture used in the present invention can be obtained from any lactide synthesis known by a person skilled in the art, starting from lactic acid and/or salts thereof and/or esters thereof or can be obtained from residues of lactide purification processes, for example distillation or crystallization in a molten medium.

In the present invention, "other impurities" means: lactic acid, other oligomers of lactic acid, the products of thermal degradation of lactic acid, esters of lactic acid and their respective oligomers, the products of thermal degradation of esters of lactic acid, the salts of lactic acid and their respective oligomers, the products of thermal degradation of salts of lactic acid, water, alcohol and residues of catalyst, for example 2-ethylhexanoic acid.

The typical starting mixture comprises between 30 and 80% of L-lactide, preferably between 40 and 70%, between 0 and 2% of water, preferably between 0 and 1%, between 5 and 50% of lactic acid and other oligomers of lactic acid ($L_nA$ with n less than or equal to 5), between 0 and 30% of the meso-lactide and between 0 and 30% of residues of catalyst such as 2-ethylhexanoic acid and/or products of thermal degradation of lactic acid.

This mixture can be derived from the purification, by crystallization in the molten state, of an impure lactide (also called raw lactide). Crystallization of the impure lactide in the molten state leads on the one hand to the formation of a purified lactide in crystalline form having a high lactide content, generally above 99%, preferably above 99.5% and a low content of the meso-lactide, generally less than 1%, preferably less than 0.5% and on the other hand to the formation of a liquid residual fraction, also called residue or drain, comprising a mixture of lactide, meso-lactide and other impurities in the proportions as described in the preceding paragraph.

In the present invention, the ether and the mixture comprising lactide, meso-lactide and other impurities are both in liquid form at the temperature of mixing between 50° C. and 90° C., preferably between 55° C. and 80° C. Once the ether is added to the mixture, the lactide precipitates instantly in the ether.

According to one embodiment of the invention, when the starting mixture contains a non-negligible amount of the meso-lactide, for example an amount greater than 10%, the ether is added to the mixture at a temperature above the temperature of precipitation of the meso-lactide in the ether, in order to avoid precipitation of the meso-lactide, and below the boiling point of the ether.

After adding the ether, the mixture can be stirred and is held at temperature, preferably above the temperature of precipitation of the meso-lactide in the ether to avoid precipitation of the latter, until complete precipitation of the lactide. The liquid phase comprises the meso-lactide and the other impurities.

Depending on the ether used, it may be necessary to cool, between 0° C. and room temperature, the mixture to which the ether was added, to precipitate the lactide. The mixture, consisting of a precipitated lactide in a liquid phase, is then separated at a low enough temperature, preferably between 15° C. and 30° C., to permit a quantitative recovery of the lactide, but not too low, in order to permit an easy removal of other impurities that are in a non-solid form.

When the lactide has precipitated in the liquid phase, the mixture is separated. Preferably, separation is carried out hot, i.e. at a temperature above the temperature of precipitation of the meso-lactide in the ether, for maximum removal of the meso-lactide from the liquid phase. Separation can be effected by any technique known by a person skilled in the art for solid/liquid separations, for example filtration, centrifugation, draining. A moist cake rich in lactide and a liquid phase are thus obtained.

The moist cake obtained after separation is then preferably dried at a product temperature below the melting point of the lactide. If the moist cake contains residual meso-lactide, the drying temperature is preferably below the melting point of the meso-lactide. Drying can for example be carried out under vacuum.

The method of the invention permits a purified lactide to be obtained having a lactide content between 80 and 99.5 wt. %.

The degree of purity of the lactide can be improved by several successive treatments of the lactide-rich cake with ether. The lactide-rich cake can be heated until it becomes liquid and treated with a new addition of ether or washed as it is, i.e. without transition to the molten state, with a new addition of ether.

Preferably, the ether used in the method of the invention is an ether of general formula $$R^1-O-R^2$$

in which $R^1$ and $R^2$ represent, independently of one another, a linear or branched alkyl or alkenyl group having from 1 to 4 carbon atoms,
an alkanol group having from 1 to 4 carbon atoms,
an aryl group,
an arylalkyl group,
a cycloalkyl group having from 4 to 6 carbon atoms
or in which $R^1$ and $R^2$ form a cyclic structure having from 2 to 6 carbon atoms.

Preferably, ethers having a total of 6 carbon atoms in the general formula described above are used, so as to facilitate extraction thereof.

Ethers such as dipropyl ether, diisopropyl ether, dibutyl ether, dipropyl ether, diethyl ether, methyl tert-butyl ether, ethyl propyl ether, ethyl tert-butyl ether, tetrahydrofuran, furan, monomethyl ether of ethylene glycol, monobutyl ether of ethylene glycol, ethylvinyl ether, dibenzyl ether, methyl amyl ether can be used in the method of the invention. Preferably, dipropyl ether, diisopropyl ether, diethyl ether and tetrahydrofuran are used.

The ether is added to the mixture in an ether/mixture weight ratio in the range from 0.5:1 to 10:1, preferably in an ether/mixture weight ratio in the range from 1:1 to 5:1. The method of the invention makes it possible to obtain a purified lactide starting from an impure lactide in liquid form by treatment of the latter with a limited amount of ether, thus making the method particularly applicable industrially, in contrast to the known methods that require dissolution of the impure lactide in the ether. These methods require the use of large quantities of ether, making it difficult to use them industrially. The use of large quantities of ether necessary for dissolving an impure lactide is described in examples given later in the application.

The liquid phase, obtained at the end of stage (d), composed of ether, meso-lactide and other impurities as defined previously, can, according to one embodiment, be sent to an extraction column or to a succession of mixer-settlers where it is brought into contact with an aqueous or other phase for recovering the meso-lactide and the other impurities (stage e).

The ether phase, after or without passing through a stage of regeneration/cleaning of the solvent (Bateman citric acid process), can be recovered for performing a new extraction of the initial mixture (stage f).

The aqueous phase comprising residual lactide, meso-lactide as well as other impurities can be recycled, if necessary after purification (resins, charcoal, filtration, etc.), upstream of lactide synthesis (stage g).

According to another embodiment of the invention, the liquid phase composed of ether, meso-lactide and other impurities obtained at the end of stage (d) of the method of the invention can be sent to a packed distillation column in which the ether is distilled at the top of the column whereas the phase laden with meso-lactide and other impurities leaves at the bottom of the column (stage e'). The latter can be hydrolysed with water to regenerate for example the lactic acid (stage f') which can be used subsequently, after purification. The ether recovered can then be used for performing a new extraction (stage g').

Whatever the embodiment described above, an improvement of the method consists, prior to stage (e) and (e'), of cooling the liquid phase composed of ether laden with impurities from stage (d) to below 30° C. until the residual lactide and meso-lactide are precipitated (stage i) and filter again so as to collect a new cake (stage ii).

The lactide resulting from the method of the invention can be purified subsequently by a process of crystallization in a molten medium in order to obtain a lactide of sufficient purity for, for example, synthesis of PLA by ring opening. In this case, the moist cake rich in lactide obtained at the end of stage (d) of the method of the invention or the dry cake obtained after drying the moist cake can be melted and recycled as the main fraction or intermediate fraction of a process for purification by crystallization in a molten medium. This option makes it possible to envisage, from an economic standpoint, industrial application of a process for purification of lactide by crystallization in a molten medium without using pre-purification by distillation of the impure lactide obtained at the end of its synthesis.

Sufficient purity implies a lactide content between 99.0 and 99.9%, preferably between 99.5 and 99.9%, a content of meso-lactide between 0 and 0.5%, preferably between 0 and 0.2%, and a water content between 0 and 100 ppm, preferably between 0 and 50 ppm.

In crystallization in a molten medium, the lactide, which can be obtained from the method of the invention, is melted and undergoes controlled cooling which initiates its crystallization (seeding with crystals is sometimes necessary) on a wall and/or directly in the melt. The impurities are thus concentrated in the liquid phase.

After the crystallization phase, the liquid phase is removed either by gravity or by any technique known by a person skilled in the art for solid/liquid separations, for example filtration, vacuum filtration, filtration under pressure or centrifugation.

For removing the film of impurities coating the surface of the crystals, more targeted technologies are required such as partial remelting of the crystals, the liquid obtained being removed by gravity or the use of a washing column, with or without forced transport, for example those mentioned in "Melt Crystallization-Fundamentals Equipment and Applications" edited by Jouchim Ulrich, Herke Glade, Shaker Verlag, 2003 and in "Melt Crystallization Technology", G. F. Arkenbout, Technomic Publishing Company Inc., 1995.

The crystals thus purified (the operation can be repeated until the required purity is attained) can then be remelted and utilized as reaction intermediate for the synthesis of PLA by ring opening. The liquid phase removed comprises a concentrate of impurities but also a non-negligible amount of lactide and meso-lactide. Treatment of this liquid phase according to the method of the invention makes it possible to extract a high proportion of the lactide and meso-lactide that are present.

EXAMPLES

In all the examples given below, the residue or drain is obtained from purification of an impure lactide by crystallization in a molten medium, and the contents of the various constituents were determined by gas chromatography after silylation of the carboxylated compounds.

Example 1

The residue or drain was treated with diisopropyl ether. For this purpose, 100 g of drain was first heated to 85° C. to obtain a drain in liquid form. 100 g of diisopropyl ether was then added and mixed with the drain. The mixture was heated at 55° C. for 1 h with stirring and was then filtered on a Buchner at 55° C. to avoid precipitation of the meso-lactide. The precipitated drain was recovered as filter cake and the diisopropyl ether as filtrate.

The precipitated drain was dried under vacuum at room temperature and the contents of the various constituents were determined. The results are presented in Table 1.

Extraction with diisopropyl ether is able to increase the content of L-lactide from 61.9 to 88.9%. The yield in recovery of L-lactide is 64.2%. The main of the meso-lactide, 2-ethylhexanoic acid, and oligomers of lactic acid are contained in the filtrate. The lactide+water complex breaks down to lactic acid dimer and also goes into the diisopropyl ether phase. This extraction with diisopropyl ether gives very good separation of the lactide from the other elements.

TABLE 1

| Constituents | Initial drain wt. % | Lactide purified after drying wt. % | Filtrate wt. % |
| --- | --- | --- | --- |
| Lactic acid | 1.7 | 0.6 | 3.6 |
| Meso-lactide | 12.3 | 2.8 | 22.2 |
| Lactic acid dimer | 2.6 | 2.2 | 9.8 |
| L-lactide | 61.9 | 88.9 | 29.4 |
| 2-Ethylhexanoic acid | 11.8 | 3.3 | 24.6 |
| Lactide + water | 5.4 | 0.2 | 0.1 |
| Lactic acid trimer | 1.7 | 0.8 | 5.5 |
| Lactic acid tetramer | 1.4 | 0.6 | 2.6 |
| Lactic acid pentamer | 1.2 | 0.6 | 2.2 |
| Enrichment, % | | +27% | |
| L-lactide yield, % (L-LD out/L-LD in) | | +64.2% | |

All of the filtrate (125.5 g) laden with lactic acid was then sent continuously to a packed distillation column. The column temperature was 118° C. at the bottom and 72° C. at the top. The diisopropyl ether was recovered at the top of the column and the phase containing the meso-lactide and other impurities was collected at the bottom of the column. Out of 125.5 g of filtrate, 43 g was collected. This phase containing lactic acid was then hydrolysed with water at 80° C. for 2 hours for recycling upstream of the lactide synthesis.

The diisopropyl ether can then be recovered for performing a new extraction of the drain.

Example 2

In this example, the purified and dried lactide obtained in Example 1 was washed with diisopropyl ether. For this, the purified lactide was mixed at room temperature with diisopropyl ether in equivalent amounts for 1 hour. The mixture was filtered at room temperature. The lactide that precipitated in the mixture was recovered as cake and was dried in conditions identical to those of Example 1

The contents of the various constituents were determined. The results are presented in Table 2.

TABLE 2

| Constituents | Purified lactide wt. % | Purified lactide after washing wt. % | Filtrate wt. % |
| --- | --- | --- | --- |
| Lactic acid | 0.6 | 0.1 | 2.1 |
| Meso-lactide | 2.8 | 2.8 | 4.6 |
| Lactic acid dimer | 2.2 | 0.5 | 12.8 |
| L-lactide | 88.9 | 95.6 | 61.5 |
| 2-Ethylhexanoic acid | 3.3 | 0.3 | 10.7 |
| Lactide + water | 0.2 | 0.1 | 0 |
| Lactic acid trimer | 0.8 | 0.1 | 4.5 |
| Lactic acid tetramer | 0.6 | 0.3 | 2 |
| Lactic acid pentamer | 0.6 | 0.2 | 1.8 |
| Enrichment, % | | +6.7% | |
| Yield of L-lactide, % (L-LD out/L-LD in) | | +67.92% | |

Examples 3 to 6

In these examples, the residue or drain was treated with diisopropyl ether at different concentrations.

For this purpose, the drain was first heated to 85° C. so as to obtain a drain in liquid form. 175 g of liquid drain was mixed respectively with 87.5 g, 175 g, 350 g and 875 g of diisopropyl ether at room temperature. After mixing, selective precipitation of the lactide present in the drain was observed. The mixture was cooled gradually to 4° C. for 1 h with stirring and was then filtered at room temperature on a Buchner. The precipitated drain was recovered as filter cake and the diisopropyl ether laden with impurities as filtrate.

The precipitated drain was then dried under vacuum at room temperature and the contents of the various constituents were determined. The results are presented in Table 3.

TABLE 3

| constituents | Drain wt. % | Example 3 IPE/drain 0.5/1 wt. % | Example 4 IPE/drain 1/1 wt. % | Example 5 IPE/drain 2/1 wt. % | Example 6 IPE/drain 5/1 wt. % |
| --- | --- | --- | --- | --- | --- |
| Lactic acid | 2.1 | 0.9 | 0.3 | 0.3 | 0.4 |
| Meso-lactide | 12.8 | 11.4 | 12.7 | 10.9 | 4.9 |
| Lactic acid dimer | 3.9 | 0.2 | 0.2 | 0.2 | 0.2 |
| L-lactide | 60.7 | 83.1 | 86.5 | 88.2 | 93.2 |
| 2-Ethylhexanoic acid | 12.7 | 1.8 | 0.3 | 0.4 | 0.6 |
| Lactide + water | 4.4 | 0.4 | 0 | 0 | 0.7 |
| Lactic acid trimer | 1.5 | 0.9 | 0 | 0 | 0 |
| Lactic acid tetramer | 1.1 | 0.7 | 0 | 0 | 0 |
| Lactic acid pentamer | 0.8 | 0.6 | 0 | 0 | 0 |
| Enrichment, % | | 22.4 | 25.8 | 27.5 | 32.5 |
| Yield L-LD, % | | 67.21 | 72.55 | 79.26 | 84.36 |

Example 7

In this example, 200 g of drain was first melted at 85° C. and then mixed with 200 g of diisopropyl ether at 60° C. After precipitation of the lactide, the mixture is filtered hot on a Buchner to recover the ether as filtrate (initial filtrate). This filtrate, with the composition shown in Table 4, was cooled to room temperature for 1 hour and then in its turn it was filtered at room temperature on a Buchner (filtrate after treatment). The contents of the various constituents of this filtrate were determined. The cake obtained after this last filtration was dried under vacuum at room temperature (lactide purified after drying) and the contents of the various constituents were determined (Table 4).

TABLE 4

| Constituents | Initial filtrate wt. % | Lactide purified after drying wt. % | Filtrate after treatment wt. % |
| --- | --- | --- | --- |
| Lactic acid | 5.3 | 0.2 | 7.9 |
| Meso-lactide | 14 | 6.2 | 15.9 |
| Lactic acid dimer | 15 | 0.3 | 29.1 |
| L-lactide | 29.4 | 91.8 | 0.5 |
| 2-Ethylhexanoic acid | 19.6 | 0.6 | 28.7 |
| Lactide + water | 0 | 0.1 | 0 |

TABLE 4-continued

| Constituents | Initial filtrate wt. % | Lactide purified after drying wt. % | Filtrate after treatment wt. % |
|---|---|---|---|
| Lactic acid trimer | 10.6 | 0.2 | 11.3 |
| Lactic acid tetramer | 3.4 | 0.3 | 3.6 |
| Lactic acid pentamer | 2.7 | 0.3 | 3 |
| Enrichment, % | | +62.4% | |
| Yield of L-lactide, % (L-LD out/L-LD in) | | +11.05% | |

Example 8

A drain was melted at 85° C. and then treated respectively with an equivalent amount of diisopropyl ether (IPE), tetrahydrofuran (THE) and 1,2-dimethoxyethane.

Extraction with IPE was performed in the same conditions as those mentioned in Example 1.

For extraction with THF, after mixing the drain with an equivalent amount of ether, the mixture was placed at −20° C. for one hour to initiate precipitation of the lactide and was then filtered. The filter cake was then dried under vacuum at room temperature.

1,2-Dimethoxyethane does not permit extraction of lactide starting from the initial drain due to lack of crystallization of the L-lactide both at room temperature and at lower temperature.

The results of the extractions with IPE and with THF are presented in Table 5.

TABLE 5

| Constituents | Initial drain wt. % | Lactide purified after drying (IPE) wt. % | Lactide purified after drying (THF) wt. % |
|---|---|---|---|
| Lactic acid | 4.5 | 0.5 | 0.1 |
| Meso-lactide | 9.4 | 2.1 | 1.3 |
| Lactic acid dimer | 8.6 | 5.5 | 0.2 |
| L-lactide | 52.0 | 89.2 | 98.1 |
| 2-Ethylhexanoic acid | 15.8 | 1.4 | 0.2 |
| Lactide + water | 3.8 | 0.2 | 0.0 |
| Lactic acid trimer | 4.6 | 0.7 | 0.1 |
| Lactic acid tetramer | 1.1 | 0.3 | 0.0 |
| Lactic acid pentamer | 0.2 | 0.1 | 0.0 |

Examples 9-10

A drain was treated with diisopropyl ether according to 2 different procedures: washing (comparative example 9) and extraction (Example 10 according to the invention).

For extraction, 100 g of drain was melted at 85° C. and then mixed with 100 g of diisopropyl ether at room temperature. The mixture was cooled gradually to 4° C. for 1 hour with stirring and then filtered at room temperature in a Buchner. The precipitated drain was dried under vacuum at room temperature and the contents of the various constituents were determined. The results are presented in Table 6.

For washing, 100 g of diisopropyl ether was added to 100 g of solid drain at room temperature. The mixture was stirred for 1 hour at room temperature and then filtered. The precipitated drain was recovered as filter cake. The filter cake was dried under vacuum at room temperature. The results are presented in Table 6.

TABLE 6

| constituents | Impure lactide wt. % | Example 9 Lactide purified after washing (comparative) wt. % | Example 10 Lactide purified after extraction (invention) wt. % |
|---|---|---|---|
| Lactic acid | 2.5 | 0.5 | 0.1 |
| Meso-lactide | 19.4 | 10.4 | 12.6 |
| Lactic acid dimer | 2.1 | 1.4 | 0.2 |
| L-lactide | 67.7 | 85.5 | 87 |
| 2-Ethylhexanoic acid | 5.3 | 0.7 | 0 |
| Lactide + water | 2.7 | 0.2 | 0.1 |
| Lactic acid trimer | 0.3 | 0.7 | 0 |
| Lactic acid tetramer | 0 | 0.5 | 0 |
| Lactic acid pentamer | 0 | 0.1 | 0 |
| Yield L-LD % | | 71.36 | 85.46 |

The yield of lactide from recovery is greater in the treatment by extraction than by washing. Washing of the drain with ether is not sufficient for purification of the lactide. The latter still contains carboxylic impurities (oligomers of lactic acid) preventing polymerization of the lactide. Moreover, it is of a yellowish appearance, in contrast to the lactide after extraction, which is white.

Example 11

In this example, a drain in solid form was mixed at room temperature with different amounts of diisopropyl ether. For this, 100 g of drain was mixed respectively with 100 g, 200 g, 500 g, 1000 g, 2000 g, 3000 g and 4000 g of diisopropyl ether. The mixture was then heated to 60° C.

No dissolution of the drain in the diisopropyl ether was observed except in the tests where the drain was in the presence of thirty and forty times more solvent. After a heating time of 6 h for both tests, partial dissolution of the drain was observed in the first case and complete dissolution of the drain was observed in the second case.

For other cases, selective precipitation of the lactide was clearly demonstrated, and it was then filtered on a Buchner and dried under vacuum at room temperature.

The invention claimed is:

1. Method of obtaining lactide starting from a mixture comprising lactide, meso-lactide, and other impurities, said method comprising the following stages:
   (a) addition of an ether to the mixture, characterized in that said mixture and the ether are both in liquid form at the temperature of mixing and in that the ether is added to the mixture in an ether/mixture weight ratio in the range from 0.5:1 to 10:1,
   (b) cooling of the mixture and of the ether obtained at the end of stage (a),
   (c) precipitation of a purified lactide in a liquid phase,
   (d) separation of the mixture obtained from stage (c) and obtention of a moist cake rich in lactide and a liquid phase.

2. Method according to claim 1, characterized in that the ether/mixture weight ratio varies between 1:1 and 5:1.

3. Method according to claim 1, characterized in that the moist cake obtained from stage (d) is dried at a product temperature below the melting point of the lactide so as to obtain a dry cake rich in lactide.

4. Method according to claim 1, characterized in that drying of the moist cake is carried out at a temperature below the melting point of the meso-lactide.

5. Method according to claim 1, comprising:
an additional stage consisting of washing the moist cake rich in lactide with ether; or
wherein the moist cake obtained from stage (d) is dried at a product temperature below the melting point of the lactide so as to obtain a dry cake rich in lactide, and washing the dry cake rich in lactide with ether.

6. Method according to claim 1, comprising:
an additional stage consisting of melting the moist cake rich in lactide and recycling it as the main fraction or intermediate fraction of a process for purification by crystallization in a molten medium; or
wherein the moist cake obtained from stage (d) is dried at a product temperature below the melting point of the lactide so as to obtain a dry cake rich in lactide, and melting the dry cake rich in lactide and recycling it as the main fraction or intermediate fraction of a process for purification by crystallization in a molten medium.

7. Method according to claim 1, characterized in that stage (d) is carried out at a temperature above the temperature of precipitation of the meso-lactide in the ether.

8. Method according to claim 1, characterized in that:
(e) the liquid phase composed of the ether laden with the meso-lactide and other impurities, obtained from stage d) after recovering the lactide-rich cake, is sent to an extraction column or a succession of mixer-settlers where it is brought into contact with an aqueous phase which recovers the meso-lactide and the other impurities from it,
(f) the ether phase after or without passing through a stage of regeneration/cleaning of the solvent is recovered for performing a new extraction of the initial mixture and
(g) the aqueous phase comprising the residual lactide, the meso-lactide and the other impurities is recycled, optionally after purification, upstream of lactide synthesis.

9. Method according to claim 1, characterized in that:
(i) the liquid phase composed of the ether laden with impurities, obtained from stage d), is cooled below 30° C. until precipitation of the residual lactide and meso-lactide occurs, and
(ii) the residual lactide and meso-lactide are filtered so as to collect a new cake and a liquid phase,
(e) the liquid phase comprising the ether obtained from stage (ii) after recovering the lactide-rich cake is sent to an extraction column or a succession of mixer-settlers where it is brought into contact with an aqueous phase, which recovers the meso-lactide and the other impurities from it,
(f) the ether phase after or without passing through a stage of regeneration/cleaning of the solvent is recovered for performing a new extraction of the initial mixture and
(g) the aqueous phase comprising the residual lactide, the meso-lactide and the other impurities is recycled, after purification, upstream of lactide synthesis.

10. Method according to claim 1, characterized in that:
(e') the liquid phase composed of ether laden with the meso-lactide and other impurities, obtained from stage d) after recovering the lactide-rich cake, is sent to a packed distillation column in which the ether is distilled at the top of the column whereas the phase laden with the meso-lactide and other impurities leaves at the bottom of the column,
(f') the phase laden with meso-lactide and other impurities obtained from stage (e') is hydrolysed with water,
(g') the ether obtained from stage (e') is recovered.

11. Method according to claim 1, characterized in that
(i) the liquid phase composed of the ether laden with impurities, obtained from stage d), is cooled below 30° C. until precipitation of the residual lactide and meso-lactide occurs, and
(ii) the residual lactide and meso-lactide are filtered so as to collect a new cake and a new liquid phase,
(e') the liquid phase comprising the ether obtained from stage (ii) after recovering the lactide-rich cake is sent to a packed distillation column in which the ether is distilled at the top of the column whereas the phase laden with meso-lactide and other impurities leaves at the bottom of the column,
(f') the phase laden with meso-lactide and other impurities obtained from stage
(e') is hydrolysed with water,
(g') the ether obtained from stage (e') is recovered.

12. Method according to claim 1, characterized in that the ether is of the general formula $$R^1-O-R^2$$

in which $R^1$ and $R^2$ represent, independently of one another, a linear or branched
alkyl or alkenyl group having from 1 to 4 carbon atoms,
an alkanol group having from 1 to 4 carbon atoms,
an aryl group,
an arylalkyl group,
a cycloalkyl group having from 4 to 6 carbon atoms
or in which $R^1$ and $R^2$ form a cyclic structure having from 2 to 6 carbon atoms.

13. Method according to claim 1, wherein the mixture is a residue or drain obtained from purification of an impure lactide by crystallization in a molten medium.

14. Method according to claim 13, wherein the residue or drain is melted to liquid form.

15. Method according to claim 1, wherein the temperature of mixing is between 50° C. and 90° C.

16. Method according to claim 1, wherein the ether is selected from the group consisting of: diisopropyl ether, dibutyl ether, dipropyl ether, methyl tert-butyl ether, ethyl propyl ether, ethyl tert-butyl ether, tetrahydrofuran, furan, monomethyl ether of ethylene glycol, monobutyl ether of ethylene glycol, ethylvinyl ether, dibenzyl ether, and methyl amyl.

17. Method according to claim 7, characterized in that stage (d) is carried out at a temperature below the boiling point of the ether.

18. Method of obtaining lactide starting from a mixture of lactide, meso-lactide, and other impurities, wherein the mixture is a melted residue or drain obtained from purification of an impure lactide by crystallization in a molten medium, said method comprising the following stages:
(a) addition of an ether to the mixture, characterized in that said mixture and the ether are both in liquid form at a temperature of mixing ranging between 50° C. and 90° C., wherein the ether is added to the mixture in an ether/mixture weight ratio in the range from 0.5:1 to 10:1,
(b) precipitation of a purified lactide in a liquid phase,
(c) separation of the mixture obtained from stage (b) and obtention of a moist cake rich in lactide and a liquid phase.

19. Method of obtaining lactide starting from a mixture comprising lactide, meso-lactide, and other impurities, said method comprising the following stages:

(a) addition of an ether to the mixture, characterized in that said mixture and the ether are both in liquid form at the temperature of mixing and in that the ether is added to the mixture in an ether/mixture weight ratio in the range from 0.5:1 to 10:1,
(b) precipitation of a purified lactide in a liquid phase,
(c) separation of the mixture obtained from stage (b) and obtention of a moist cake rich in lactide and a liquid phase.

20. Method according to claim 19, wherein the ether is selected from the group consisting of: diisopropyl ether, dibutyl ether, dipropyl ether, methyl tert-butyl ether, ethyl propyl ether, ethyl tert-butyl ether, tetrahydrofuran, furan, monomethyl ether of ethylene glycol, monobutyl ether of ethylene glycol, ethylvinyl ether, dibenzyl ether, and methyl amyl.

* * * * *